(12) United States Patent
Dale-Crunk et al.

(10) Patent No.: US 7,700,308 B2
(45) Date of Patent: Apr. 20, 2010

(54) METHODS FOR DETERMINING SUSCEPTIBILITY TO DENTAL CARIES

(75) Inventors: Beverly A. Dale-Crunk, Ellensburg, WA (US); Janet R. Kimball, Seattle, WA (US); Renchuan Tao, Guangxi (CN)

(73) Assignee: University of Washington, Seattle, WA (US)

( * ) Notice: Subject to any disclaimer, the term of this patent is extended or adjusted under 35 U.S.C. 154(b) by 1153 days.

(21) Appl. No.: 11/214,474

(22) Filed: Aug. 29, 2005

(65) Prior Publication Data

US 2006/0057654 A1 Mar. 16, 2006

Related U.S. Application Data

(60) Provisional application No. 60/610,579, filed on Sep. 16, 2004.

(51) Int. Cl.
*G01N 33/569* (2006.01)
*G01N 33/53* (2006.01)

(52) U.S. Cl. ........................................ 435/7.32; 435/7.1

(58) Field of Classification Search .................. 435/7.32
See application file for complete search history.

(56) References Cited

U.S. PATENT DOCUMENTS 7,309,759 B2 * 12/2007 Krieger et al. .............. 530/300

OTHER PUBLICATIONS

Goebel et al. "Peptides, vol. 21, pp. 757-765 , 2000".*
Sequence alignment for Seq ID No. 1 .*
Burgess et al. (J of Cell Biology, 1990 vol. 111, pp. 2129-2138).*
Lazar et al (Molecular and Cellular Biology, 1988, vol. 8, pp. 1247-1252).*
Mizukawa et al. (Oral Surgery Oral Medicine Oral Pathology vol. 87, No. 5, May 1999).*
Dale et al. ( Jouranl of Oral Pathol. Med. vol. 30, pp. 321-327, Feb. 2001).*
Bals, R., and J.M. Wilson, "Cathelicidins—A Family of Multifunctional Antimicrobial Peptides," *Cell Mol. Life Sci.* 60:711-720, 2003.
Bonass, W.A., et al., "Expression of β-Defensin Genes by Human Salivary Glands," *Oral Microbiol. Immunol.* 14:371-374, 1999.
Dale, B.A., and L.P. Fredericks, *Antimicrobial Peptides in Human Health and Disease*, Horizon Scientific Press, Hethersett, United Kingdom, 2001, Chap. 8, "Antimicrobial Peptides in the Oral Environment: Expression and Function in Health and Disease," pp. 223-252.
Dale, B.A., and S. Krisanaprakornkit, "Defensin Antimicrobial Peptides in the Oral Cavity," *J. Oral Pathol. Med.* 30:321-327, 2001.
Dale, B.A., et al., "Localized Antimicrobial Peptide Expression in Human Gingiva," *J. Periodont. Res.* 36:285-294, 2001.
Dunsche, A., et al., "The Novel Human Beta-Defensin-3 Is Widely Expressed in Oral Tissues," *Eur. J. Oral Sci.* 109:121-124, 2002.
Ganz, T., "Defensins: Antimicrobial Peptides of Innate Immunity," *Nat. Rev. Immunol.* 3:710-720, 2003.
Ganz, T., et al., "Definsins: Natural Peptide Antibiotics of Human Neutrophils," *J. Clin. Invest.* 76:1427-1435, 1985.
Hicks, J., et al., "Biological Factors in Dental Caries: Role of Saliva and Dental Plaque in the Dynamic Process of Demineralization and Remineralization (Part 1)," *J. Clin. Pediatr. Dent.* 28(1):47-52, 2003.
Hollox, E.J., et al., "Extensive Normal Copy Number Variation of a β-Defensin Antimicrobial-Gene Cluster," *Am. J. Hum. Genet.* 73:591-600, 2003.
Joly, S., et al., "Human β-Defensins 2 and 3 Demonstrate Strain-Selective Activity Against Oral Microorganisms," *J. Clin. Microbiol.* 42(3):1024-1029, 2004.
Linzmeier, R.M., and T. Ganz, "Human Defensin Gene Copy Polymorphisms: Comprehensive Analysis of Independent Variation in α- and β-Defensin Regions at 8p. 22-p. 23," *Genomics*, 2005 <http://www.sciencedirect.com>.
Loesche, W.J., "Role of *Streptococcus mutans* in Human Dental Decay," *Microbiol. Rev.* 50(4):353-380, 1986.
Maisetta, G., et al., "Activity of Human β-Defensin 3 Alone or Combined With Other Antimicrobial Agents Against Oral Bacteria," *Antimicrob. Agents Chemother.* 47(10):3349-3351, 2003.
Mars, W.M., et al., "Inheritance of Unequal Numbers of the Genes Encoding the Human Neutrophil Defensins HP-1 and HP-3," *J. Biol. Chem.* 270(51):30371-30376, 1995.
McKay, M.S., et al., "Immunomagnetic Recovery of Human Neutrophil Defensins From the Human Gingival Crevice," *Oral Microbiol. Immunol.* 14:190-193, 1999.
Murakami, M., et al., "Cathelicidin Antimicrobial Peptides Are Expressed in Salivary Glands and Saliva," *J. Dental Res.* 81(12):845-850, 2002.
Nagaoka, I., et al., "Synergistic Actions of Antibacterial Neutrophil Defensins and Cathelicidins," *Inflamm. Res.* 49:73-79, 2000.
Nishimura, E., et al., "Oral *Streptococci* Exhibit Diverse Susceptibility to Human β-Defensin-2: Antimicrobial Effects of hBD-2 on Oral *Streptococci*," *Curr. Microbiol.* 48:85-87, 2004.
Sahasrabudhe, K.S., et al., "Expression of the Antimicrobial Peptide, Human β-Defensin 1, in Duct Cells of Minor Salivary Glands and Detection in Saliva," *J. Dental. Res.* 79(9):1669-1674, 2000.
Selsted, M.E., and A.J. Ouellette, "Mammalian Defensins in the Antimicrobial Immune Response," *Nat. Immunol.* 6(6):551-557, 2005.
Tanaka, D., et al., "Sensitivity of *Actinobacillus actinomycetemcomitans* and *Capnocytophaga* spp. to the Bactericidal Action of LL-37: A Cathelicidin Found in Human Leukocytes and Epithelium," *Oral Microbiol. Immunol.* 15:226-231, 2000.
An Nieuw Amerongen, A., et al., "Salivary Proteins: Protective and Diagnostic Value in Cariology?" *Caries Res.* 38:247-253, 2004.

(Continued)

*Primary Examiner*—Robert Mondesi
*Assistant Examiner*—Khatol Shahnan-Shah
(74) *Attorney, Agent, or Firm*—Christensen O'Connor Johnson Kindness PLLC

(57) ABSTRACT

The present invention provides methods for determining whether a human being is susceptible to dental caries. The methods each include the steps of measuring the amount of α-defensins HNP 1, HNP 2 and HNP 3 in saliva obtained from a human being, and determining whether a reduced amount of the α-defensins HNP 1, HNP 2 and HNP 3 is present in the saliva, thereby determining whether the human being is susceptible to dental caries.

13 Claims, No Drawings

OTHER PUBLICATIONS

Woo, J-S., et al., "Expression of Cathelicidin in Human Salivary Glands," *Arch. Otolaryngol. Head Neck Surg.* 129:211-214, 2003.

Yang, D., et al., "Multiple Roles of Antimicrobial Defensins, Cathelicidins, and Eosinophil-Derived Neurotoxin in Host Defense," *Annual Rev. Immunol.* 22:181-215, 2004.

Zasloff, M., "Antimicrobial Peptides of Multicellular Organisms," *Nature* 415:389-395, 2002.

Zhao, C., et al., "Widespread Expression of Beta-Defensin hBD-1 in Human Secretory Glands and Epithelial Cells," *FEBS Letters* 396:319-322, 1996.

* cited by examiner

METHODS FOR DETERMINING SUSCEPTIBILITY TO DENTAL CARIES

CROSS-REFERENCE TO RELATED APPLICATION

This application claims the benefit under 35 U.S.C. §119 (e) of U.S. Provisional Patent Application No. 60/610,579, filed Sep. 16, 2004.

STATEMENT OF GOVERNMENT LICENSE RIGHTS

The U.S. Government has a paid-up license in this invention and the right in limited circumstances to require the patent owner to license others on reasonable terms as provided for by the terms of Grant No. U54DE14254 awarded by the National Institutes of Health/National Institute of Dental and Craniofacial Research.

FIELD OF THE INVENTION

The present invention relates to methods for determining whether a human being is susceptible to tooth decay.

BACKGROUND OF THE INVENTION

Dental caries is a common disease process that afflicts a large proportion of the world population. Extensive research indicates that dental caries is the result of a bacterial infection (Loesche, W. J., *Microbiol. Rev.* 50:353-380, 1986), but is also influenced by host and dietary factors (Hicks, J., et al., *J. Clin. Pediatr. Dent.* 28:47-52, 2003). Current research seeks to identify risk factors for caries, and to identify natural oral defenses that may protect against, or prevent, caries development. Salivary defense systems play a significant role in maintaining the health of the oral cavity and preventing caries. These defenses include factors which inhibit or reverse demineralization of exposed tooth surfaces, such as simple mechanical rinsing, buffering action, and calcium phosphate binding proteins, as well as antimicrobial activities including microorganism aggregation and clearance from the oral cavity, immune surveillance, and the secretion of antimicrobial peptides (Van Nieuw Amerongen, A., et al., *Caries Res.* 38:247-253, 2004).

Antimicrobial peptides (AMPs) are natural antibiotics that provide a first line of defense against a wide spectrum of pathogens (Ganz, T., *Nat. Rev. Immunol.* 3:710-720, 2003; Yang, D., et al., *Annual Rev. Immunol.* 22:181-215, 2004; Zasloff, M., *Nature* 415:389-395, 2002). The three main AMP families are defined by amino acid composition and three-dimensional structure: α-helical peptides without cysteine (the cathelicidins) (Bals, R., et al., *Cell Mol. Life Sci.* 60:711-720, 2003); peptides with three disulphide bonds (the α- and β-defensins) (Ganz, T., *Nat. Rev. Immunol.* 3:710-720, 2003; Ganz, T., et al., *J. Clin. Invest.* 76:1427-1435, 1985); and peptides with an unusually high proportion of specific amino acids, for example, the histatins (Oppenheim, F. G., et al., *J. Biol. Chem.* 263:7472-7477, 1988).

The human β-defensins (hBDs) are widely expressed in oral tissues and in gingival epithelium (Dale, B. A., et al., *J. Periodontal Res.* 36:285-294, 2001; Dunsche, A., et al., *Eur. J. Oral Sci.* 110:121-124, 2002; Zhao, C., et al., *FEBS Letters* 396:319-322, 1996). HBD1 and 2 have also been detected in salivary glands and ducts and in saliva (Bonass, W. A., et al., *Oral Microbiol. Immunol.* 14:371-374, 1999; Sahasrabudhe, K. S., et al., *J. Dental Res.* 79:1669-1674, 2000). The α-defensins, HNP 1, HNP 2, and HNP 3, are expressed in neutrophils, and participate in non-oxidative microbial death (Ganz, T., et al., *J. Clin. Invest.* 76:1427-1435, 1985), and have been identified in gingival crevicular fluid (McKay, M. S., et al., *Oral Microbiol. Immunol.* 14:190-193, 1999). The human cathelicidin peptide, LL37, is found in neutrophils and inflamed epithelia as well as in saliva (Murakami, M., et al., *J. Dental Res.* 81:845-850, 2002). Both the mRNA and protein for cathelicidin peptides have been localized to the salivary glands, specifically in acinar cells of the submandibular gland and palatine minor glands, as well as in lingual epithelium and palatal mucosa in mice (Murakami, M., et al., *J. Dental Res.* 81:845-850, 2002) and submandibular duct cells in humans (Woo, J. S., et al., *Arch. Otolaryngol Head Neck Surg.* 129:211-214, 2003).

The defensins and cathelicidins have broad antimicrobial activity against Gram-negative and Gram-positive bacteria and *Candida albicans*, and are effective, in vitro, against oral microorganisms such as *Streptococcus mutans*, *Porphyromonas gingivalis* and *Actinobacillus actinomycetemcomitans* (Dale, B. A., et al., in R. L. Gallo (ed.), *Horizon Bioscience*, pp. 223-251, Wymondham, 2004; Joly, S., et al., *J. Clin. Microbiol.* 42:1024-1029, 2004; Nishimura, E., et al., *Curr. Microbiol.* 48:85-87, 2004; Tanaka, D., et al., *Oral Microbiol. Immunol.* 15:226-231, 2000). The cathelicidins and α- and β-defensins act synergistically with other antimicrobials (Maisetta, G., et al., *Antimicrob. Agents Chemother.* 47:3349-3351, 2003; Nagaoka, I., et al., *Inflamm. Res.* 49:73-79, 2000).

Despite improved knowledge of the various antimicrobial agents present in human saliva, there remains a need for methods to identify human beings who are susceptible to dental caries, and who will likely benefit from prophylactic measures to prevent tooth decay.

SUMMARY OF THE INVENTION

The present inventors have discovered that the total amount of three α-defensin peptides, HNP 1, HNP 2 and HNP 3, in saliva correlate with the susceptibility of a human being to dental caries. The combined amount of the HNP 1, HNP 2 and HNP 3 peptides is lower than normal in saliva of human beings susceptible to dental caries. Conversely, the combined amount of the HNP 1, HNP 2 and HNP 3 peptides is higher than normal in saliva of human beings resistant to dental caries. Thus, measurement of the amount of the HNP 1, HNP 2 and HNP 3 peptides in saliva of a human being can be used to determine the susceptibility of a human being to dental caries. This information can be used to identify those people who are at increased risk for dental caries and who require additional dental treatment to prevent, or slow, the development of dental caries (e.g., improved oral hygiene, use of antiseptic mouthwashes, periodic treatment with concentrated fluoride solutions, increased frequency of visits to an oral hygienist).

Thus, in one aspect, the present invention provides methods for determining whether a human being is susceptible to dental caries. The methods of this aspect of the invention each include the steps of measuring the amount of α-defensins HNP 1, HNP 2 and HNP 3 in saliva obtained from a human being, and determining whether a reduced amount of the α-defensins HNP 1, HNP 2 and HNP 3 is present in the saliva, thereby determining whether the human being is susceptible to dental caries. A reduced amount of α-defensins HNP 1, HNP 2 and HNP 3 in the saliva indicates susceptibility of the human being to dental caries.

DETAILED DESCRIPTION OF THE PREFERRED EMBODIMENT

In one aspect, the present invention provides methods for determining whether a human being is susceptible to dental caries. The methods each include the steps of measuring the amount of α-defensins HNP 1, HNP 2, and HNP 3 in saliva obtained from a human being, and determining whether a reduced amount of the α-defensins HNP 1, HNP 2, and HNP 3 is present in the saliva, thereby determining whether the human being is susceptible to dental caries. In this regard, a reduced amount of the α-defensins HNP 1, HNP 2, and HNP 3 in the saliva indicates susceptibility of the human being to dental caries. Conversely, an elevated amount of the α-defensins HNP 1, HNP 2, and HNP 3 in the saliva indicates resistance of the human being to dental caries.

The term "dental caries" refers to erosion and/or decay of a tooth (or teeth) caused by bacteria in the mouth.

The term "α-defensin", or "alpha defensin", refers to a member of a family of peptides that possess antibiotic activity. α-defensins are made within the body by neutrophils (a type of white blood cell) and macrophages (cells that can engulf foreign particles). While not wishing to be bound by theory, it is believed that α-defensins exert their antimicrobial effect by binding to the outer membrane(s) of bacteria and fungi, thereby permeabilizing the membranes. Alpha-defensins are described, for example, by Ganz, T., "Defensins: Antimicrobial Peptides of Innate Immunity," *Nat. Rev. Immunol.* 3:710-720, 2003, and by Selsted, M. E., and A. J. Ouellette, "Mammalian Defensins in the Antimicrobial Immune Response," *Nat. Immunol.* 6:551-557, 2005, both of which publications are incorporated herein by reference.

In the practice of the present invention, the amount of α-defensins HNP 1, HNP 2, and HNP 3 is measured to determine whether a human being is susceptible to dental caries. The amount of α-defensins HNP 1, HNP 2, and HNP 3 is the sum of the individual amounts of α-defensins HNP 1, HNP 2, and HNP 3. The individual amounts of α-defensins HNP 1, HNP 2, and HNP 3 can be measured separately, and the individual amounts added together to produce the amount of α-defensins HNP 1, HNP 2, and HNP 3; or the amount of α-defensins HNP 1, HNP 2, and HNP 3 can be determined in a single measurement (e.g., by using an antibody that binds to all of the HNP 1, HNP 2, and HNP 3 peptides). The amount of α-defensins HNP 1, HNP 2, and HNP 3 can be expressed as a concentration, such as μg per milliliter saliva, or μg per milligram total salivary protein.

HNP 1, HNP 2, and HNP 3 peptides useful in the practice of the present invention are each at least 70% identical (e.g., at least 80% identical, or at least 90% identical, or at least 95% identical, or at least 99% identical) to the representative, human, HNP 1 amino acid sequence set forth in SEQ ID NO:1. The amino acid sequence of the precursor that includes the representative HNP 1 (SEQ ID NO:1) is publicly available at the website of the National Center for Biotechnology Information, U.S. National Library of Medicine, 8600 Rockville Pike, Bethesda, Md. 20894, USA, under GenBank Accession No. A40499.

Sequence identity (typically expressed as percent identity) in the context of two peptide sequences refers to the number of amino acid residues in the two sequences that are the same when aligned for maximum correspondence over a specified comparison window. Sequence identity values provided herein refer to the value obtained using GAP (e.g., GCG programs, version 10, (Accelrys, Inc., San Diego, Calif.)) using the following parameters: percent identity using GAP weight of 50 and length weight of 3; the entire amino acid sequence of a candidate peptide and a reference peptide are compared. An equivalent method to GAP may be used. The term "equivalent method" refers to any sequence comparison method, such as a sequence comparison program, that, for any two sequences in question, generates an alignment having identical amino acid residue matches and an identical percent sequence identity when compared to the corresponding alignment generated by GAP.

GAP uses the algorithm of Needleman & Wunsch *J. Mol. Biol.* 48:443-453, 1970, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. Default gap creation penalty values and gap extension penalty values in Version 10 of the Wisconsin Genetics Software Package for peptide sequences are 8 and 2, respectively.

The combined amount of α-defensins HNP 1, HNP 2, and HNP 3 can be measured using any useful method. For example, the amount of α-defensins HNP 1, HNP 2, and HNP 3 can be measured using an Enzyme Linked Immunoassay (abbreviated as ELISA). A sandwich-style ELISA is preferred in which the standards and unknowns are incubated in microtiter wells pre-coated with antibody that captures the α-defensins. The samples (e.g., saliva samples) and standards are diluted (typically at least 1/2000) in a buffer containing detergent for 1 hour at room temperature prior to loading the microtiter wells. The captured α-defensins are then detected with tracer-linker antibody (e.g., biotinylated second antibody) that binds to each of HNP 1, HNP 2, and HNP 3 which is then detected, for example by using a streptavidin-peroxidase conjugate and colored substrate (e.g., TMB). If TMB is used as the colored substrate then color development is measured at a wavelength of 450 nanometers. The concentration of HNP 1, HNP 2, and HNP 3 in experimental samples is determined using a standard curve prepared from known combined concentrations of HNP 1, HNP 2, and HNP 3 peptides. This type of sandwich ELISA can measure HNP 1-3 concentrations between 40 pg/ml and 10,000 pg/ml.

Again by way of example, mass spectrometry (abbreviated as MS), such as Surface Enhanced Laser Desorption/Ionization Mass Spectrometry (abbreviated as SELDI-MS), or Matrix Associated Laser Desorption Ionization Time of Flight Mass Spectrometry (abbreviated as MALDI-TOF MS), procedures can be used to measure the combined amount of HNP 1, HNP 2, and HNP 3 peptides. In brief, in the practice of the SELDI-MS method, diluted samples or standards are adsorbed onto a hydrophilic chip surface, unbound components are washed away, and an MS matrix material added and dried. Mass analysis is performed by time-of-flight (TOF) mass spectrometry, for example using a CIPHERGEN™ system instrument (see, e.g., Diamond, D. L., et al., *J. Immunolog. Meth.* 256:65-76, 2001). The masses of HNP 1, HNP 2, and HNP 3, as measured using the SELDI-MS method, are typically 3442, 3371, and 3486 Da, respectively, although minor variations in these masses may be observed in some individuals.

With respect to MALDI-TOF, samples can be mixed with matrix material and directly analyzed, for example as described by Uttenweiler-Joseph, S. et al. (*Proc. Natl. Acad. Sci., USA* 95:11342-11347, 1998), or by Lundy, F. T., et al.

(*Molec. Immunol.* 42:575-579, 2005), both of which publications are incorporated herein by reference.

Other techniques for measuring the combined amount of HNP 1, HNP 2, and HNP 3 peptides in saliva include High Pressure Liquid Chromatography (abbreviated as HPLC), dot immunoassay and the combination of gel electrophoresis with western blot. These methods for measuring the combined amount of HNP 1, HNP 2, and HNP 3 peptides in saliva require acid-extraction of the saliva sample prior to assay. Aliquots (e.g., 200 µl) of saliva sample are acid extracted by the addition of an equal volume of 1M HCl/1% trifluoroacetic acid (TFA), and the acidified samples are mixed overnight in the cold (e.g., at a temperature of 4° C.) (Murakami, M., et al., *J. Dental Res.* 81:845-850, 2002). The sample is then centrifuged and the supernatant concentrated (e.g., by vacuum evaporation) and resuspended in an amount of distilled water equal to the starting sample volume.

In the practice of a representative HPLC method for measuring the combined amount of HNP 1, HNP 2, and HNP 3 peptides in saliva, the acidified saliva sample is diluted in 0.1% trifluoroacetic acid, filtered through a 0.2 micron, low protein binding filter to remove particulate matter, then separated on a C18 reverse phase column. The sample is eluted with a gradient from 1-80% of 0.1% trifluoroacetic acid in acetonitrile. Time of elution is determined by comparison with HNP 1, HNP 2, and HNP 3 peptide standards.

In the practice of a representative dot immunoassay method for measuring the combined amount of HNP 1, HNP 2 and HNP 3 peptides in saliva, serial dilution of the saliva samples and standards are dotted in triplicate on nitrocellulose membrane. Excess protein binding sites are blocked with 10% nonfat dried milk and buffered-saline at room temperature for at least 2 hours. The membrane is incubated with rabbit antibody, that reacts with all of HNP 1, HNP 2, and HNP 3 peptides, overnight at 4° C., then washed and incubated with goat-antirabbit immunoglobulin conjugated with horseradish peroxidase. Bound antibody is detected using a chemiluminescence reagent, and the signal is quantified by densitometric analysis (see, e.g., Ong, P. Y., et al., *N. Engl. J. Med.* 347:1151-1160, 2002, which publication is incorporated herein by reference).

In the practice of a representative western blot method for measuring the combined amount of HNP 1, HNP 2, and HNP 3 peptides in saliva, acidified samples and standards are mixed with sodium dodecyl sulfate (abbreviated as SDS), boiled, and separated by electrophoresis on 16.5% SDS-tricine polyacrylamide gels. Samples are transferred to nitrocellulose membranes, fixed for 30 minutes with buffered formaldehyde, blocked with 10% nonfat dried milk and treated the same way as in the dot immunoassay method described supra. Detection is with chemiluminescence reagent, and the signal is quantified by densitometric analysis.

In the practice of the present invention, the presence of a reduced amount of the HNP 1, HNP 2, and HNP 3 peptides in the saliva of a human being indicates susceptibility of the human being to dental caries. A "reduced amount" of HNP 1, HNP 2, and HNP 3 peptides is an amount of HNP 1, HNP 2, and HNP 3 peptides in human saliva that is statistically significantly less than a normal amount (or normal range of amounts) of HNP 1, HNP 2, and HNP 3 peptides in human saliva. A normal amount (or normal range of amounts) of HNP 1, HNP 2, and HNP 3 peptides in human saliva can be determined using experimental design and statistical techniques known to those skilled in the art. Example 1 herein provides an example of a study that determined, inter alia, a normal range for the amount of HNP 1, HNP 2, and HNP 3 peptides in human saliva.

In some embodiments of the present invention, an amount of HNP 1, HNP 2, and HNP 3 peptides in the saliva less than 0.4 µg per milliliter saliva indicates susceptibility of the human being to dental caries. In some embodiments of the present invention, an amount of HNP 1, HNP 2, and HNP 3 peptides in the saliva less than 0.3 µg per milliliter saliva indicates susceptibility of the human being to dental caries. In some embodiments of the present invention, an amount of HNP 1, HNP 2, and HNP 3 peptides in the saliva less than 0.2 µg per milliliter saliva indicates susceptibility of the human being to dental caries. In some embodiments of the present invention, an amount of HNP 1, HNP 2, and HNP 3 peptides in the saliva less than 0.1 µg per milliliter saliva indicates susceptibility of the human being to dental caries.

In some embodiments of the present invention, an amount of HNP 1, HNP 2, and HNP 3 peptides in the saliva less than 0.3 µg per milligram total salivary protein indicates susceptibility of the human being to dental caries. In some embodiments of the present invention, an amount of HNP 1, HNP 2, and HNP 3 peptides in the saliva less than 0.2 µg per milligram total salivary protein indicates susceptibility of the human being to dental caries. In some embodiments of the present invention, an amount of α-defensin peptides in the saliva less than 0.1 µg per milligram total salivary protein indicates susceptibility of the human being to dental caries.

The following examples merely illustrate the best mode now contemplated for practicing the invention, but should not be construed to limit the invention. All literature citations herein are expressly incorporated by reference.

EXAMPLE 1

This Example shows that the median concentrations of the α-defensin peptides HNP1, HNP2, and HNP3 in saliva are significantly higher in children with no dental caries than in children with dental caries.

Participants and Oral Examination. One hundred and forty-nine children participated in the study. A brief health history survey was completed by parents of the subjects. Oral examinations were performed by trained calibrated clinicians using standardized procedures. The study was conducted with permission of school officials and informed consent of subjects and parents obtained through an educational session and written bilingual consent in accordance with a protocol approved by the University of Washington Institutional Review Board. Examiners were instructed to rank subjects separately for active caries and for filled surfaces as 0, no decayed or filled surfaces; 1, mild (1-2 affected surfaces); 2, moderate (3-6 affected surfaces); and 3, severe (>6 affected surfaces). Final caries experience score was determined as the sum of the scores for active decay and filled surfaces. Oral examinations and sample collection were conducted over a two day period primarily in the morning.

Salivary analysis. Unstimulated saliva was collected (3-5 ml), the detergent NONIDET-40™ (Sigma, St. Louis, Mo.) was added to a final concentration of 0.1%, and the sample was frozen for later analysis. Saliva was thawed and cleared by centrifugation twice at 15,000 rpm for 10 min. Total protein concentration was evaluated in the supernatant (cleared unfractionated saliva) by BCA assay (Pierce Inc., Rockford, Ill., USA). Cleared unfractionated saliva was also used for the HNP1-3 ELISA assay according to manufacturer's instructions (HyCult Biotechnology, Uden, Netherlands). Aliquots (200 μl) of supernatant were acid-extracted by the addition of an equal volume of 1M HCl/1% TFA overnight with mixing in the cold (Murakami, M., et al., *J. Dental Res.* 81:845-50, 2002). The sample was centrifuged and the supernatant was concentrated by vacuum evaporation and resuspended in distilled water equal to the starting sample volume. Acid extracted saliva was used for immunoassay of LL37 and hBD3. LL37 was assayed by slot blot using an assay kit (Phoenix Pharmaceuticals Inc., Belmont, Calif.) HBD3 was assayed by slot blot using polyclonal antibody to hBD3 (Orbigen Inc., San Diego, Calif.) Peptide standard for hBD3 was from Peptides International, Inc. (Louisville, Ky.) Statistical analysis for association of antimicrobial peptide levels with caries score was done using the Kruskal-Wallis non-parametric test based on rank and designed for non-normally distributed data.

Immunohistochemistry. Formalin-fixed sections were evaluated for expression of HNP1-3 using the ABC technique (Vector Laboratories, Burlingame, Calif.) Briefly, sections were deparaffinized, rehydrated, and treated with antigen unmasking solution (Vector Laboratories). Endogenous peroxide was blocked using 1% hydrogen peroxide/Tris-buffered saline for 30 min. Sections were blocked with appropriate sera and incubated with the primary antibody overnight before visualizing with ABC reagents using 3,3' diaminobenzidine as substrate. Methyl green counterstain (KPL, Gaithersburg, Md.) was used to visualize tissue morphology. Sections were also stained for expression of LL-37 for comparison. The antibodies used were polyclonal rabbit anti-LL37 (Phoenix Pharmaceuticals, Inc., Belmont, Calif.) and monoclonal antibody clone D21 anti-HNP1-3 (Cell Sciences, Canton, Mass.) Monoclonal antibody clone D21 bound to each of the HNP 1, HNP 2 and HNP 3 peptides. Commercially available histological sections of human submandibular glands were from Spring Biosciences (Fremont, Calif.)

Demographics and Caries Experience. Eighty-eight females and 61 males participated in the study. All children were between 11 and 15 years of age. Most of the population was Hispanic with some Native Americans and Caucasians. Overall, the children were healthy with 92% having no history of major illness or disease. The most commonly reported medication was for asthma. One subject reported current use of an antibiotic. Oral examination showed that 80% of the children had permanent dentition, 20% had mixed dentition, 6% had missing teeth, and 11% had loose teeth. 65% of the population reported having regular dental care. Gingivitis was noted in only a small number of subjects (<5); one subject had a stainless steel crown and two subjects had orthodontics appliances. Fifty-three subjects (36%) had no decay, 37 (24%), 39 (27%), and 20 (13%) had caries scores of 1, 2, and 3 or greater, respectively.

Salivary analysis. The median protein concentration of unstimulated saliva samples (n=144) was 1485 μg/ml (range from 421 to 7052 μg/ml). The salivary protein concentration showed no correlation with age, gender, or caries score. This value agrees with previously reported total protein concentration for this age group (Ben-Aryeh, H., et al., *Arch Oral Biol.* 35:929-31, 1990). AMP concentrations were in the μg/ml range. AMP levels were also normalized to the protein concentration in whole saliva for each sample. Results are summarized in Table 1.

TABLE 1

SALIVARY ANTIMICROBIAL PEPTIDE LEVELS

| Peptide | Sample Number | Median | 25%-75% | Min | Max |
|---|---|---|---|---|---|
| Concentration (μg/ml) | | | | | |
| HNP1-3 | 143 | 0.61 | 0.39-1.09 | 0.06 | 10.50 |
| LL37 | 128 | 3.07 | 1.72-4.83 | 0.12 | 12.0 |
| HBD3 | 133 | 0.31 | 0.10-0.89 | 0 | 6.21 |
| Total protein | 144 | 1485 | 1101-1905 | 421 | 7052 |
| Concentration relative to total salivary protein (μg/mg salivary protein) | | | | | |
| HNP1-3 | 143 | 0.43 | 0.25-0.74 | 0.04 | 6.96 |
| LL37 | 127 | 2.29 | 1.05-3.15 | 0.07 | 25.33 |
| HBD3 | 133 | 0.23 | 0.06-0.68 | 0 | 4.36 |

HNP1-3 (an abbreviation for HNP 1, HNP 2, and HNP 3), hBD3, and LL37 all showed extensive variation in concentration in the population, even when normalized to total salivary protein levels. Median values for HNP1-3, hBD3, and LL37 were 0.61, 0.31, 3.07 μg/ml, respectively.

Relationship of salivary AMPs and caries experience. In order to evaluate the relationship of AMP expression and caries experience in the population, we used the Kruskal-Wallis non-parametric test based on rank. We found a significant difference in the amount of HNP1-3 among different caries groups (p=0.004). Differences were observed for both the median level of salivary HNP1-3 concentration (μg/ml) and salivary HNP1-3 relative to salivary protein (μg/mg). The median HNP1-3 concentration was 0.89 μg/ml (with an interquartile range of 0.5-1.4) for the caries free group (n=51), and 0.5 μg/ml (0.24-0.9 interquartile range) for all subjects with evidence of caries (n=90). The HNP1-3 value relative to total salivary protein was 0.67 μg/mg protein (0.38-0.93) in the caries free group and 0.33 μg/mg protein (0.19-0.59) in the combined caries group (p=0.004). The results showed the same trend with higher levels of LL37 in the no caries group than in those with caries, but results were not statistically significant. HBD3 concentration in saliva and the level of hBD3 relative to protein showed no significant difference among the population or between the different caries groups.

Additional analyses showed that HNP1-3 concentration was positively correlated with total salivary protein (Spearman's rank correlation (r=0.239, p<0.001). As suggested above, HNP1-3 was negatively correlated with Caries Score (r=−0.281), and the correlation was significant at the 0.001 level (p=0.001).

To further examine the relationship between the amount of HNP1-3 and caries development, the concentration of HNP1-3 was evaluated in subjects with no caries compared to those with caries. An increasing proportion of subjects had no caries as the HNP concentration increased; 90% of the subjects with HNP1-3 levels of ≦0.25 μg/ml (n=26) had caries, but only 47% of the subjects with HNP1-3 levels greater than 1.0 μg/ml (n=38) had caries.

Immunohistochemical ocalization of AMPs. The presence of HNP1-3 in saliva, especially in some individuals with levels more than twice the median concentration, and its overall greater level in caries-free children, was unexpected. There was no evidence that those with high HNP1-3 had loose teeth which might lead to the presence of increased blood and neutrophils in their saliva which would be expected to contribute to elevated HNP1 -3. To clarify the possible source of AMPs in saliva, immunohistochemistry was performed in commercially available histological sections of human submandibular glands (Spring Biosciences, Fremont, Calif.) Positive immunohistochemical reaction for both HNP1-3 and LL37 was seen in duct cells in submandibular glands and in minor salivary glands. As expected, neutrophils in these biopsies stained positively for HNP1-3 and LL37. No staining for HNP1-3 was detected in the mucosal epithelium present in the same biopsies, while, in contrast, strong reaction for LL37 was found in the mucosal epithelium.

Results: HNP1-3, LL37, and hBD3 are all detectable in saliva but show extensive variation in concentration between subjects. The concentration of AMPs in unstimulated saliva of children has not been previously reported, although normal adults had a mean value of 0.8 µg/ml HNP1-3 (Mizukawa, N., et al., *Oral Surg. Oral Med. Oral Pathol. Oral Radiol. Endod.* fensins in saliva could be due to previously demonstrated polymorphisms in sequence and copy number in the genes encoding these peptides (Hollox, E. J., et al., *Am. J. Hum Genet* 73:591-600, 2003; Mars, W. M., et al., *J. Biol. Chem.* 270:30371-6, 1995; Linzmeier, R. M., and Ganz, T., "Human Defensin Gene Copy Number Polymorphisms: Comprehensive Analysis of Independent Variation in A- and B-Defensin Regions at 8p22-P23" *Genomics,* 2005 (article available online Jul. 20, 2005), as well as to variations in neutrophil efflux via the gingival fluid.

While the preferred embodiment of the invention has been illustrated and described, it will be appreciated that various changes can be made therein without departing from the spirit and scope of the invention.

```
SEQUENCE LISTING

<160> NUMBER OF SEQ ID NOS: 1

<210> SEQ ID NO 1
<211> LENGTH: 30
<212> TYPE: PRT
<213> ORGANISM: Homo sapiens

<400> SEQUENCE: 1

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30
```

87:539-43, 1999). Salivary HNP1-3 is significantly greater in caries-free children than in those with caries. HNP1-3 is detectable in salivary duct cells, suggesting that salivary glands express α-defensins as well as β-defensins and LL37.

Within the oral cavity, LL37 and β-defensins are expressed in oral epithelial tissues including salivary glands (Bonass, W. A., et al., *Oral Microbiol. Immunol.* 14:371-4, 1999; Dale, B. A., et al., in R. L. Gallo (ed.), *Horizon Bioscience,* 223-251, Wymondham, 2004; Dunsche, A., et al., *Eur. J. Oral Sci* 110:121-4, 2002; Murakami, M., et al., *J. Dental Res.* 81:845-50, 2002; Woo, J. S., et al., *Arch. Otolaryngol. Head Neck Surg.* 129:211-214, 2003). In addition, the experiments described in this Example show expression of HNP1-3 by immunohistochemistry in submandibular salivary duct cells. The presence of both HNP1-3 and LL37 in submandibular glands, which are the major source of unstimulated saliva, suggests that these cells may be a source of AMPs in saliva. An additional source for both of these peptides in saliva are the neutrophils that migrate into the oral cavity via gingival crevicular fluid. In normal individuals it has been estimated that 30,000 neutrophils per minute enter the oral cavity via this route through the junctional epithelium surrounding the teeth (Schroeder, H. E., *The Periodontium,* Springer-Verlag, Berlin, 1986). The present results suggest that both neutrophils and duct cells are a source of HNP1-3 and that α-defensins are part of the extensive antimicrobial armamentarium of saliva.

Salivary AMP concentrations showed large variation between individuals, with a significantly higher level of salivary α-defensins, HNP1-3, in children with no caries. The salivary levels of HNP1-3 antimicrobial peptides may represent a genetically determined factor that contributes to caries susceptibility. The large variation in concentration of α-de- The embodiments of the invention in which an exclusive property or privilege is claimed are defined as follows:

1. A method of determining whether a human child is susceptible to dental caries, the method comprising the steps of:
    (a) measuring the amount of α-defensins HNP 1, HNP 2 and HNP 3 in saliva obtained from a human child; and
    (b) comparing the measured amount of the α-defensins HNP 1, HNP 2 and HNP 3 to a reference value, wherein an amount less than a reference value of 0.4 µg of HNP 1, HNP 2 and HNP 3 per milliliter of saliva indicates the human child is susceptible to dental caries.

2. A method of claim 1, wherein the amount of α-defensins HNP 1, HNP 2 and HNP 3 is measured using a method selected from the group consisting of enzyme linked immunoassay, mass spectrometry, high pressure liquid chromatography, dot immunoassay and a combination of gel electrophoresis and western blot.

3. A method of claim 1, wherein the amount of α-defensins HNP 1, HNP 2 and HNP 3 is measured using an enzyme linked immunoassay.

4. A method of claim 1, wherein the α-defensins HNP 1, HNP 2 and HNP 3 are each at least 90% identical to an HNP 1 α-defensin peptide consisting of the amino acid sequence set forth in SEQ ID NO:1.

5. A method of claim 1, wherein the α-defensins HNP 1, HNP 2 and HNP 3 are each at least 95% identical to an HNP 1 α-defensin peptide consisting of the amino acid sequence set forth in SEQ ID NO:1.

6. A method of claim 1, wherein the α-defensins HNP 1, HNP 2 and HNP 3 are each at least 99% identical to an HNP 1 α-defensin peptide consisting of the amino acid sequence set forth in SEQ ID NO:1.

7. A method of claim 1, wherein an amount of the HNP 1, HNP 2 and HNP 3 peptides less than 0.3 μg per milliliter saliva indicates susceptibility of the human child to dental caries.

8. A method of claim 1, wherein an amount of the HNP 1, HNP 2 and HNP 3 peptides less than 0.2 μg per milliliter saliva indicates susceptibility of the human child to dental caries.

9. A method of claim 1, wherein an amount of the HNP 1, HNP 2 and HNP 3 peptides less than 0.1 μg per milliliter saliva indicates susceptibility of the human child to dental caries.

10. A method of claim 1, wherein an amount of the HNP 1, HNP 2 and HNP 3 peptides less than 0.3 μg per milligram total salivary protein indicates susceptibility of the human child to dental caries.

11. A method of claim 1, wherein an amount of the HNP 1, HNP 2 and HNP 3 peptides less than 0.2 μg per milligram total salivary protein indicates susceptibility of the human child to dental caries.

12. A method of claim 1, wherein an amount of the HNP 1, HNP 2 and HNP 3 peptides less than 0.1 μg per milligram total salivary protein indicates susceptibility of the human child to dental caries.

13. A method of claim 1, wherein the saliva obtained is unstimulated saliva.

\* \* \* \* \*

UNITED STATES PATENT AND TRADEMARK OFFICE
CERTIFICATE OF CORRECTION

PATENT NO. : 7,700,308 B2
APPLICATION NO. : 11/214474
DATED : April 20, 2010
INVENTOR(S) : Dale-Crunk et al.

Page 1 of 1

It is certified that error appears in the above-identified patent and that said Letters Patent is hereby corrected as shown below:

| COLUMN | LINES | |
|---|---|---|
| 1 | 7-9 | "The U.S. Government has a paid-up license in this invention and the right in limited circumstances to require the patent owner to license others on reasonable terms as provided for by the terms of Grant No. U54DE14254 awarded by the National Institutes of Health/National Institute of Dental and Craniofacial Research." should read --This invention was made with government support under grant number U54DE14254 awarded by the National Institutes of Health, The Government has certain rights in the invention.-- |

Signed and Sealed this

Twentieth Day of December, 2011

David J. Kappos
*Director of the United States Patent and Trademark Office*